(12) United States Patent
Papenbrock et al.

(10) Patent No.: US 11,065,082 B2
(45) Date of Patent: Jul. 20, 2021

(54) TREATMENT METHOD FOR A SERVICE WATER SUPPLY UNIT

(71) Applicant: BLUE SAFETY GMBH, Münster (DE)

(72) Inventors: Jan Papenbrock, Münster (DE); Sebastian Fischer, Münster (DE); Christian Mönninghoff, Münster (DE)

(73) Assignee: BLUE SAFETY GMBH, Münster (DE)

(*) Notice: Subject to any disclaimer, the term of this patent is extended or adjusted under 35 U.S.C. 154(b) by 536 days.

(21) Appl. No.: 15/767,061

(22) PCT Filed: Oct. 10, 2016

(86) PCT No.: PCT/EP2016/074237
§ 371 (c)(1),
(2) Date: Apr. 9, 2018

(87) PCT Pub. No.: WO2017/060532
PCT Pub. Date: Apr. 13, 2017

(65) Prior Publication Data
US 2018/0296304 A1    Oct. 18, 2018

(30) Foreign Application Priority Data

Oct. 9, 2015   (DE) .................. 10 2015 219 659.3

(51) Int. Cl.
*A61C 1/00*      (2006.01)
*A61C 19/00*     (2006.01)
(Continued)

(52) U.S. Cl.
CPC .......... *A61C 1/0076* (2013.01); *A61C 1/0084* (2013.01); *A61C 19/002* (2013.01);
(Continued)

(58) Field of Classification Search
CPC ....... A61L 2/16; A61C 1/0076; A61C 19/002; B08B 1/002; B08B 1/006; B08B 9/021; B08B 9/027
See application file for complete search history.

(56) References Cited

U.S. PATENT DOCUMENTS 6,106,854 A * 8/2000 Belfer ................. A01N 59/00
                                                            424/405
6,107,097 A    8/2000 Pfeifer
(Continued)

FOREIGN PATENT DOCUMENTS

CN    102353549 A    2/2012
CN    103920684 A    7/2014
(Continued)

OTHER PUBLICATIONS

English Language Machine Translation for EP 1186574, Mar. 2002 (Year: 2002).*
(Continued)

*Primary Examiner* — Sean E Conley
(74) *Attorney, Agent, or Firm* — Norris McLaughlin, P.A.

(57) ABSTRACT

Method for treating a service water supply unit of a dental treatment unit, wherein the method has the following sequence of treatment steps: cleaning the service water supply unit using a cleaning agent, preferably a cleaning liquid or a cleaning foam; disinfecting the service water supply unit using a disinfecting agent, preferably a disinfecting liquid.

13 Claims, 8 Drawing Sheets

(51) Int. Cl.
| | |
|---|---|
| *A61L 2/16* | (2006.01) |
| *B08B 1/00* | (2006.01) |
| *B08B 9/02* | (2006.01) |
| *B08B 9/027* | (2006.01) |
| *B08B 9/20* | (2006.01) |
| *B08B 3/10* | (2006.01) |
| *A61L 2/18* | (2006.01) |
| *B08B 3/02* | (2006.01) |
| *B08B 3/08* | (2006.01) |

(52) U.S. Cl.
CPC .................. *A61L 2/16* (2013.01); *A61L 2/18* (2013.01); *B08B 1/002* (2013.01); *B08B 1/006* (2013.01); *B08B 9/021* (2013.01); *B08B 9/027* (2013.01); *B08B 9/20* (2013.01); *A61L 2202/17* (2013.01); *A61L 2202/24* (2013.01); *B08B 3/02* (2013.01); *B08B 3/08* (2013.01); *B08B 3/10* (2013.01)

(56) References Cited

U.S. PATENT DOCUMENTS

| | | |
|---|---|---|
| 6,619,302 B2 | 9/2003 | Labib et al. |
| 2001/0047813 A1 | 12/2001 | Labib et al. |
| 2012/0010750 A1 | 1/2012 | Wahl et al. |
| 2018/0177565 A1 | 6/2018 | Papenbrock et al. |
| 2018/0296304 A1 | 10/2018 | Papenbrock et al. |

FOREIGN PATENT DOCUMENTS

| | | |
|---|---|---|
| DE | 100 59 987 A1 | 8/2001 |
| DE | 10 2015 212 248 A1 | 1/2017 |
| DE | 10 2015 219 659 A1 | 4/2017 |
| EP | 0 886 778 B1 | 12/1998 |
| EP | 1 186 574 A1 | 3/2002 |
| EP | 1 260 281 A2 | 11/2002 |
| JP | 2008-302231 A1 | 12/2018 |
| WO | 99/48817 A2 | 9/1999 |
| WO | WO 99/48817 * | 9/1999 |

OTHER PUBLICATIONS

International Search Report dated Jan. 11, 2017, dated Jan. 20, 2017.

English translation of International Search Report dated Jan. 11, 2017, dated Jan. 20, 2017.

DIN 10516, "Food Hygiene—Cleaning and Disinfection" May 2009.

Office Action dated Jan. 13, 2021, in connection with Chinese Application No. 201680071766.6.

Office Action dated Mar. 29, 2021, in connection with Japanese Application No. 2018-518493.

\* cited by examiner

TREATMENT METHOD FOR A SERVICE WATER SUPPLY UNIT

This application is the U.S. National Stage of International Application No. PCT/EP2016/074237, filed Oct. 10, 2016, which claims foreign priority benefit under 35 U.S.C. § 119 of German Application No. 10 2015 219 659.3 filed Oct. 9, 2015.

The present invention relates to a service water supply unit for dental treatment units. The dental treatment unit may be or include a rotating instrument in the form of a drill. The service water provided by the service water supply unit is typically used for cooling the instrument and for rinsing a patient's oral cavity.

A service water supply unit which is particularly suitable for dental treatment units may comprise a pressurized water vessel together with a vessel receptacle for accommodating a pressurized water vessel, having a compressed air inlet for connecting the service water supply unit to a compressed air source, a compressed air port via which compressed air originating from the compressed air inlet can be introduced into the pressurized water vessel, and having a service water port via which the service water which is to be delivered from the pressurized water vessel by the compressed air introduced into the pressurized water vessel can be dispensed to the dental treatment unit.

Such a service water supply unit which additionally has a sterile air filter is for example described in the as yet unpublished German patent application with the file reference 10 2015 212 248.4.

However, a service water supply unit for dental treatment units does not necessarily have a pressurized water vessel. Instead, a service water supply unit may also be a free outlet as defined for example in standard DIN EN 1717.

As defined therein, a free outlet is a permanently unimpeded free flow section, either outside or within the supplied dental treatment unit, between the inlet-side outlet orifice of the drinking water installation and the outlet-side service water, measured at maximum service water level. The outlet-side service water is preferably stored in a service water reservoir. The dental treatment unit is typically supplied with service water by means of a pump or compressed air.

It is the object of the present invention to increase the operational capability with regard to hygiene of a service water supply unit for dental treatment units.

Said object is achieved by a method for treating a service water supply unit of a dental treatment unit, wherein the method has the following sequence of treatment steps:
 cleaning the service water supply unit using a cleaning agent, preferably a cleaning liquid or a cleaning foam, preferably thereafter
 disinfecting the service water supply unit using a disinfecting agent, preferably a disinfecting liquid.

The method is preferably carried out manually. The method can be carried out by machine and for example saved in the form of a program sequence plan for a machine.

The invention encompasses the recognition that service water supply units for dental treatment units are medical devices or components of medical devices which should be operated with low levels of microbial contamination. The service water supply units can namely be contaminated by microorganisms and thus pose a non-negligible risk of infection which can even result in death.

The invention likewise encompasses the recognition that there have hitherto been no methods which increase the operational capability with regard to hygiene of the service water supply unit by reducing the risk of infection for service water supply units, in particular those of the initially stated type having a vessel receptacle and pressurized water vessel. At most, the prior art discloses, in relation to service water supply units, test methods with which process water treatment methods of the service water supply units can be microbially validated.

The sequence of treatment steps according to the invention overcomes these disadvantages. In particular for service water supply units of the initially stated type having a vessel receptacle and pressurized water vessel, the advantage arises that the pressurized water vessel, which previously had to be disposed of in the event of microbial contamination, can be put to further use.

In a preferred configuration, the service water supply unit comprises a pressurized water vessel together with a vessel receptacle for accommodating a pressurized water vessel, having a compressed air inlet for connecting the service water supply unit to a compressed air source, a compressed air port via which compressed air originating from the compressed air inlet can be introduced into the pressurized water vessel, and having a service water port via which the service water which is to be delivered from the pressurized water vessel by the compressed air introduced into the pressurized water vessel can be dispensed to the dental treatment unit.

The sequence of treatment steps is preferably further developed in that the vessel receptacle and/or the pressurized water vessel is cleaned using a cleaning agent, preferably a cleaning liquid or a cleaning foam, and then the vessel receptacle and/or pressurized water vessel is disinfected using a disinfecting agent, preferably a disinfecting liquid.

Cleaning may at least in part proceed mechanically. Cleaning preferably includes wiping, scrubbing and/or brushing, which is preferably repeated a number of times. Cleaning particularly preferably proceeds by means of a cloth, rag or sponge or by means of a brush, preferably impregnated or provided with the cleaning agent.

Cleaning may proceed with a flowing or stationary cleaning agent, preferably within a cleaning tank.

In a particularly preferred configuration of the method, the cleaning agent is an alkaline cleaning agent which preferably has a pH of between 7 and 10, preferably at its application concentration. The cleaning agent furthermore preferably has no fixing characteristics, which permits the advantage of simple handling with reduced use of personal protective equipment and is thus very cost-effective and gentle on materials and the skin.

The cleaning agent may be a combination cleaning agent, in particular providing said combination cleaning agent is not a disinfecting cleaning product.

Any residues of the cleaning agent used during mechanical cleaning are preferably rinsed off by means of a rinsing liquid in the course of the method after mechanical cleaning and before disinfection.

It has proved advantageous for the rinsing liquid to be sterile, in particular autoclaved or filtered, distilled, bidistilled or deionized water. The cleaning agent preferably includes sterile, in particular autoclaved or filtered, distilled, bidistilled or deionized water.

In a particularly preferred configuration, disinfection of the pressurized water vessel proceeds by means of immersion disinfection. The method preferably includes placing the pressurized water vessel into a disinfection tank filled with the disinfecting agent such that the pressurized water vessel is completely covered by the disinfecting agent and an interior volume of the pressurized water vessel remains free of air bubbles. The disinfecting agent is then preferably allowed to act for a contact time. The contact time may for example amount to less than 30 minutes. The pressurized water vessel is then preferably removed from the disinfection tank.

It has proved particularly advantageous for disinfection of the pressurized water vessel to proceed by means of internal filling level disinfection. This may include completely filling an interior volume of the pressurized water vessel with the disinfecting agent, allowing the disinfecting agent to act for a contact time, and/or emptying the interior volume of the pressurized water vessel.

The disinfecting agent, in particular the disinfecting agent intended for internal disinfection, is advantageously selected from the group or includes one or more substances from the following group: aldehydes, aldehyde releasers, alkylamines or alkylamine derivatives, amphoteric surfactants, inorganic acids, chlorine-releasing compounds, chloramides, glycol derivatives, guanidines or guanidine derivatives, iodine-releasing compounds, alkalies, organic acids, peroxide compounds, phenols or phenol derivatives, phenol ethers, pyridine derivatives, quaternary compounds, heavy metal compounds, metal compounds or thiocyanates.

The disinfecting agent used preferably does not have a fixing action. The disinfecting agent should preferably be based on one of the active ingredients or active ingredient combinations or for example from one of the active substance groups which are listed in the following table.

| | |
|---|---|
| Aldehydes | 2-ethyl-1-hexanal, formaldehyde, glutardialdehyde, glyoxal, o-phthalic dialdehyde, succinaldehyde |
| Aldehyde releasers | 2-alkoxy-3,4-dihydro-2-H-pyran, 1,6-dihydroxy-2,5-dioxohexane, formacetal, dimethoxytetrahydrofuran, ethylene glycol bisformaldehyde, polymethylolurea derivatives |
| Alcohols | benzyl alcohol, 1,3-butanediol, ethanol, 2-ethyl-1-hexanol, methoxyisopropanol, 1-propanol, 2-propanol |
| Alkylamines or alkylamine derivatives | alkylamines, bis(3-aminopropyl)dodecylamine, n-cocopropylenediammonium borate dodecylamine sulfamate, n-3-dodecylaminopropyl glycine, n-dodecyl-n-(3-aminopropyl) 1,3-propanediamine, glucoprotamine |
| Amphoteric surfactants | alkyl oligoaminocarboxylic acid |
| Inorganic acid | phosphoric acid |
| Chlorine-releasing compounds | organic chlorine carriers |
| Chloramides | chloramine-T [tosylchloramide sodium] |
| Glycol derivatives | diethylene glycol monomethyl ether, phenoxyethanol, phenoxypropanol, propylene glycol |
| Guanidines (or guanidine derivatives) | alkyl biguanide, chlorhexidine digluconate, cocopropylenediamine guanidinium diacetate, oligomeric biguanide, polyhexamethylene biguanide hydrochloride [oligodiiminoimidocarbonyl iminohexamethylene, polyhexanide] |
| Iodine-releasing compounds | poly(1-vinyl-2-pyrrolidone)-iodine complex |
| Alkalies | alkali metal hydroxides |
| Organic acids | formic acid, malic acid, benzoic acid, glyoxylic acid, lactic acid, undecanoic acid, tartaric acid, citric acid |
| Peroxide compounds | potassium peroxymonosulfate, magnesium monoperphthalate, sodium perborate, peracetic acid, hydrogen peroxide |
| Phenols or phenol derivatives | 2-biphenylol, 2-benzyl-4-chlorophenol, 4-chloro-3-methylphenol, chloroxylenol, 3,3'-dibromo-5,5'-dichloro-2,2'-dihydroxydiphenylmethane [bromochlorophen], dibromo-4-hydroxybenzenesulfonic acid, 2-methyl-3,4,5,6-tetrabromophenol, 2-oxydiphenyl, 2,3,4,5-tetrabromo-6-methylphenol |
| Phenol ethers | 2,4,4-trichloro-2-hydroxydiphenyl ether [triclosan] |
| Pyridine derivatives | octenidine dihydrochloride, bispyridine |
| Quaternary compounds | alkyl didecylpolyoxethylammonium propionate, alkyl dimethylalkylbenzylammonium chloride, alkyl dimethylethylammonium chloride, alkyl dimethylethylbenzylammonium chloride, benzalkonium propionate, benzalkonium chloride [alkyl dimethylbenzylammonium chloride, cocodimethylbenzylammonium chloride, lauryldimethylbenzylammonium chloride, myristyldimethylbenzylammonium chloride], benzethonium chloride, benzyldihydroxyethylcocoalkylammonium chloride, cocodimethylbenzylammonium chloride, dialkyldimethylammonium chloride [didecyldimethylammonium chloride], |

-continued

| | |
|---|---|
| | didecylmethyloxyethylammonium propionate, mecetronium ethylsulfate, methylbenzethonium chloride, n-octyldimethylbenzylammonium chloride, undecylamidopropyltrimonium methosulfate |
| Heavy metal compounds, metal compounds | tri-n-butyltin benzoate, silver |
| Thiocyanates | potassium thiocyanate |

The working solution may be present in a concentration of between 0.5% and 5% or, in the case of the alcohol active substance group, in the concentrated form of the sales solution.

The disinfecting agent may be an alcohol-based disinfecting agent. The alcohol content may be greater than 50%.

It has proven advantageous for the disinfection of the pressurized water vessel to proceed by means of external spraying or wiping disinfection and preferably to involve spraying the exterior surface of the pressurized water vessel with the disinfecting agent. Disinfection may include allowing the disinfecting agent to act for a contact time. Disinfection may include wiping the exterior surface of the pressurized water vessel by means of a cloth, rag or sponge or by means of a brush, preferably impregnated or provided with the disinfecting agent.

Preferably, during cleaning and/or during disinfection of the vessel receptacle, preferably in this order, an interior underside of the vessel receptacle, which in proper operation faces the pressurized water vessel and from which the service water port projects, is treated, an interior side face of the vessel receptacle, which in proper operation faces the pressurized water vessel and rests against the latter and does not include the service water port, is treated, and/or the service water port and the compressed air port are treated.

Preferably, during cleaning and/or during disinfection of the pressurized water vessel, preferably in this order, an exterior face of the pressurized water vessel, which face in proper operation faces the vessel receptacle and into which the service water port projects, is treated, an exterior side face of the pressurized water vessel, which side face in proper operation faces the pressurized water vessel and rests against the latter, is treated, and/or an interior volume of the pressurized water vessel is treated, preferably beginning with an interior bottom of the pressurized water vessel.

It has proven advantageous for the sequence of treatment steps to be repeated after at most one month of operation of the service water supply unit. The sequence is preferably repeated after at most 400 operating hours, preferably at most 360 operating hours, particularly preferably after at most 300 operating hours.

The object is likewise achieved by a method for defining a sequence of treatment steps for treating a service water supply unit, wherein the method has the steps:
providing a service water supply unit of a dental treatment unit, specifying a group of defined test points,
selecting at least one of, preferably a plurality of, the test points actually present on the service water supply unit from the specified group of defined test points,
selecting a first test point to be tested from the subgroup of the plurality of test points actually present on the service water supply unit, to which a relevance criterion applies,
applying a defined test soil, in particular a protein test soil and/or a bacterial test soil, to the first test point to be tested,
subjecting the first test point to be tested to a cleaning step which is selected from a specified group of treatment steps, wherein the cleaning step is carried out with a specified cleaning duration and a specified cleaning intensity, and then,
subjecting the first test point to be tested to a disinfection step which is selected from the specified group of treatment steps, wherein the disinfection step is carried out with a specified disinfection duration and a specified disinfection concentration,
detecting a reduction in the test soil at the test point,
documenting or saving the sequence of the cleaning step carried out with a specified cleaning duration and a specified cleaning intensity and the disinfection step carried out with a specified disinfection duration and a specified disinfection concentration, preferably in a database, if the detected reduction falls below a specified threshold.

The respectively selected cleaning step and/or the respective disinfection step is preferably excluded from the group of treatment steps if the detected reduction does not fall below a specified threshold.

The group of treatment steps from which a selection is to be made for the purposes of defining a sequence of treatment steps at least includes not only the disinfection steps/disinfection methods described with reference to the method for treating the service water supply unit but also the cleaning steps/cleaning methods described with reference to the method for treating the service water supply unit.

The method is preferably configured iteratively such that, if the detected reduction does not fall below a specified threshold, a defined test soil is once again applied to the first or respectively further test point and another cleaning step and/or another disinfection step is then carried out for the first or further test point.

The relevance criterion is preferably one of the following properties of the test point: water-conveying, contact with water spray, contact with water splashes, contact with condensation water, contact with atmospheric humidity, indentations, grooves or dead zone.

In a preferred configuration, the cleaning duration, cleaning intensity, disinfection duration and/or disinfection concentration is/are increased if the detected reduction does not fall below a specified threshold.

Furthermore preferably, the cleaning duration and/or cleaning intensity are increased and/or the cleaning method changed if the detected reduction in a protein test soil does not fall below a specified threshold.

It has proven advantageous for the disinfection duration and/or disinfection concentration and/or disinfection method to be increased if the detected reduction in a bacterial test soil does not fall below a specified threshold.

It is particularly preferred for the specified threshold to correspond to a reduction by at least 4 log steps, preferably 5 log steps.

The group of defined test points preferably includes the following test points: internal walls of tubes, internal faces of tanks, external faces of tanks, seals, valves, disinfecting agent metering system, filters, particulate filters, retrogradely contaminable/contaminated open vessel systems, retrogradely contaminable/contaminated tube systems, grooves, indentations, connectors, receiving devices, closures, inner walls of vessels, inner walls of pressure vessels, outer walls of vessels, outer walls of pressure vessels, threaded closures, threaded connectors, threads, push fittings, valve membranes, pumps, pump membranes, dead flow zones, surfaces, nozzles or push-fit nozzles.

For the purposes of the method for defining a sequence of treatment steps for treating a service water supply unit, the service water supply unit preferably comprises a pressurized water vessel together with a vessel receptacle for accommodating a pressurized water vessel, having a compressed air inlet for connecting the service water supply unit to a compressed air source, a compressed air port via which compressed air originating from the compressed air inlet can be introduced into the pressurized water vessel, and having a service water port via which the service water which is to be delivered from the pressurized water vessel by the compressed air introduced into the pressurized water vessel can be dispensed to the dental treatment unit.

The object is likewise achieved by a method for defining a sequence of treatment steps for treating a service water supply unit, wherein the method has the steps:

providing a service water supply unit of a dental treatment unit, specifying a group of defined test points, selecting a first test point to be tested from the group to which a relevance criterion applies, applying a defined test soil, in particular a protein test soil and/or a bacterial test soil, to the first test point to be tested, subjecting the first test point to be tested to a (respective) cleaning step which is selected from a specified group of treatment steps, wherein the cleaning step is carried out with a specified cleaning duration and a specified cleaning intensity, and then, subjecting the first test point to be tested to a disinfection step which is selected from the specified group of treatment steps, wherein the disinfection step is carried out with a specified disinfection duration and a specified disinfection concentration, detecting a reduction in the test soil at the test point, documenting or saving the sequence of the cleaning step carried out with a specified cleaning duration and a specified cleaning intensity and the disinfection step carried out with a specified disinfection duration and a specified disinfection concentration, preferably in a database, if the detected reduction falls below a specified threshold.

The relevance criterion is preferably one of the following properties of the test point: water-conveying, contact with water spray, contact with water splashes, contact with condensation water, contact with atmospheric humidity, indentations, grooves or dead zone.

In a preferred configuration of the method, the respectively selected cleaning step and/or the respective disinfection step is excluded from the group of treatment steps if the detected reduction does not fall below a specified threshold. Advantageously, a defined test soil, in particular a protein test soil and/or a bacterial test soil, is then once again applied to the first test point to be tested.

The first test point to be tested may then be subjected to a different/modified cleaning step, wherein the cleaning step is selected from a specified group of remaining treatment steps and wherein the cleaning step is preferably carried out with a specified cleaning duration and a specified cleaning intensity.

The first test point to be tested is then preferably subjected to a different/modified disinfection step which is selected from the specified group of remaining treatment steps. The disinfection step can be carried out with a specified disinfection duration and a specified disinfection concentration.

In a preferred configuration, a reduction in the test soil at the test point is subsequently detected once again and the step of documenting or saving the sequence of the cleaning step carried out with a specified cleaning duration and a specified cleaning intensity and the disinfection step carried out with a specified disinfection duration and a specified disinfection concentration, preferably in a database, is preferably carried out once again if the detected reduction falls below a specified threshold.

A second test point to be tested can then be selected from the subgroup of the plurality of test points actually present on the service water supply unit to which the same or another relevance criterion applies.

It has proven advantageous for the method to provide an increase in the cleaning duration and/or cleaning intensity and/or a change in the cleaning method if the detected reduction in a protein test soil does not fall below a specified threshold.

It has likewise proven advantageous for the method to provide an increase in the disinfection duration and/or disinfection concentration and/or disinfection method if the detected reduction in a bacterial test soil does not fall below a specified threshold. The specified threshold particularly preferably corresponds to a reduction by at least 4 log steps, preferably 5 log steps.

The group of defined test points can include the following test points: internal walls of tubes, internal faces of tanks, external faces of tanks, disinfecting agent metering system, seals, valves, filters, particulate filters, retrogradely contaminable/contaminated open vessel systems, retrogradely contaminable/contaminated tube systems, grooves, indentations, connectors, receiving devices, closures, inner walls of vessels, inner walls of pressure vessels, outer walls of vessels, outer walls of pressure vessels, threaded closures, threaded connectors, threads, push fittings, valve membranes, pumps, pump membranes, dead flow zones, surfaces, nozzles or push-fit nozzles.

In an advantageous configuration of the method, the cleaning duration, cleaning intensity, disinfection duration and/or disinfection concentration is/are increased if the detected reduction does not fall below a specified threshold.

The method for defining a sequence of treatment steps for treating a service water supply unit of a dental treatment unit is preferably carried out on a service water supply unit which comprises a pressurized water vessel together with a vessel receptacle for accommodating a pressurized water vessel, having a compressed air inlet for connecting the service water supply unit to a compressed air source, a compressed air port via which compressed air originating from the compressed air inlet can be introduced into the pressurized water vessel, and having a service water port via which the service water which is to be delivered from the pressurized water vessel by the compressed air introduced into the pressurized water vessel can be dispensed to the dental treatment unit.

The method can be correspondingly further developed by features which are described with reference to the method for treating a service water supply unit.

Exemplary embodiments of the invention are now described below with reference to the drawings. Further advantages, features and details of the invention are revealed by the following description of the preferred exemplary embodiments with reference to the drawings, in which.

Figure 1:
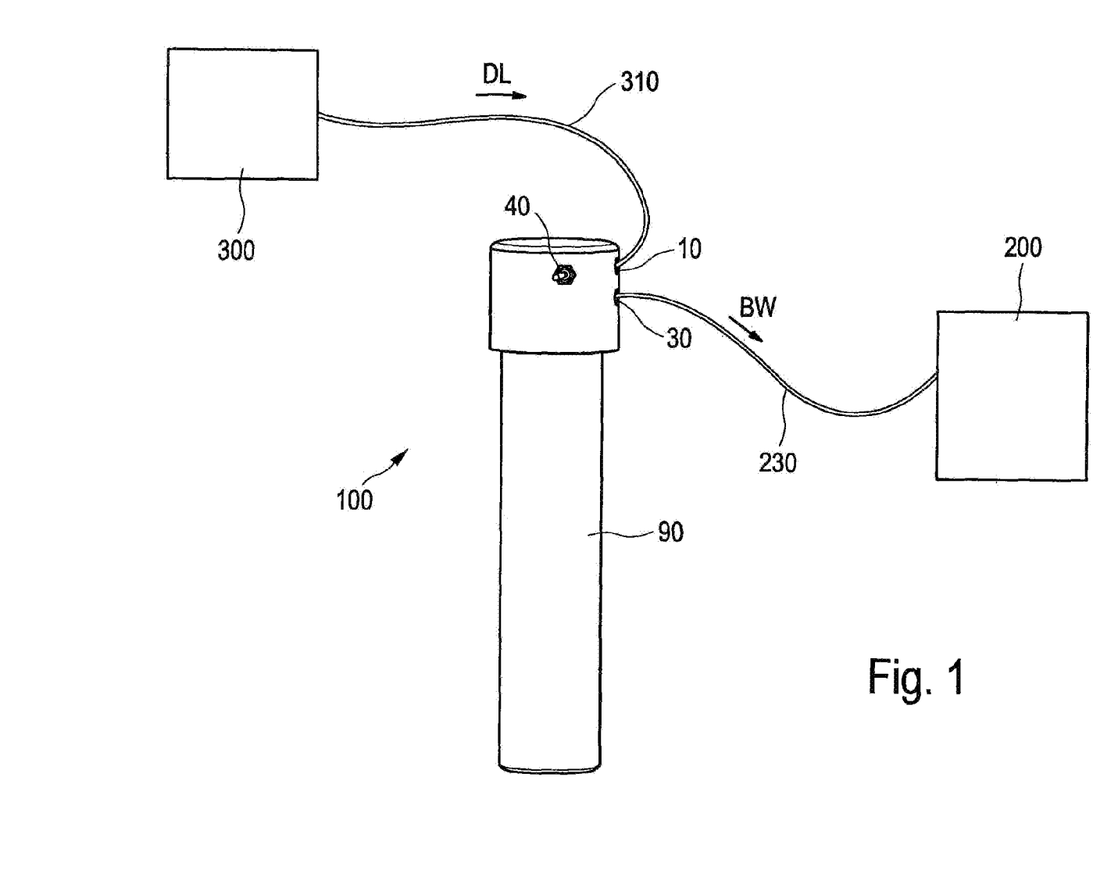
FIG. 1 is a schematic representation of a service water supply unit in which the methods according to the invention are preferably to be applied.

FIG. 1 shows a service water supply unit 100 in the form of a "bottle" system which is connected to a dental treatment unit 200 and a compressed air source 300. A compressed air source 300 in the form of a compressor is connected via a compressed air feed line 310 to the compressed air inlet 10 of the service water supply unit 100, such that compressed air DL originating from the compressed air source 300 can flow into the compressed air inlet 10.

By means of the introduced compressed air DL, service water BW located in the pressurized water vessel 90 is supplied via a service water feed line 230 of the medical treatment unit 200, in the present case a dental unit. In the medical treatment unit 200 provided as a dental unit, the service water BW is in turn supplied to a drill or a rinsing head.

Figure 2:
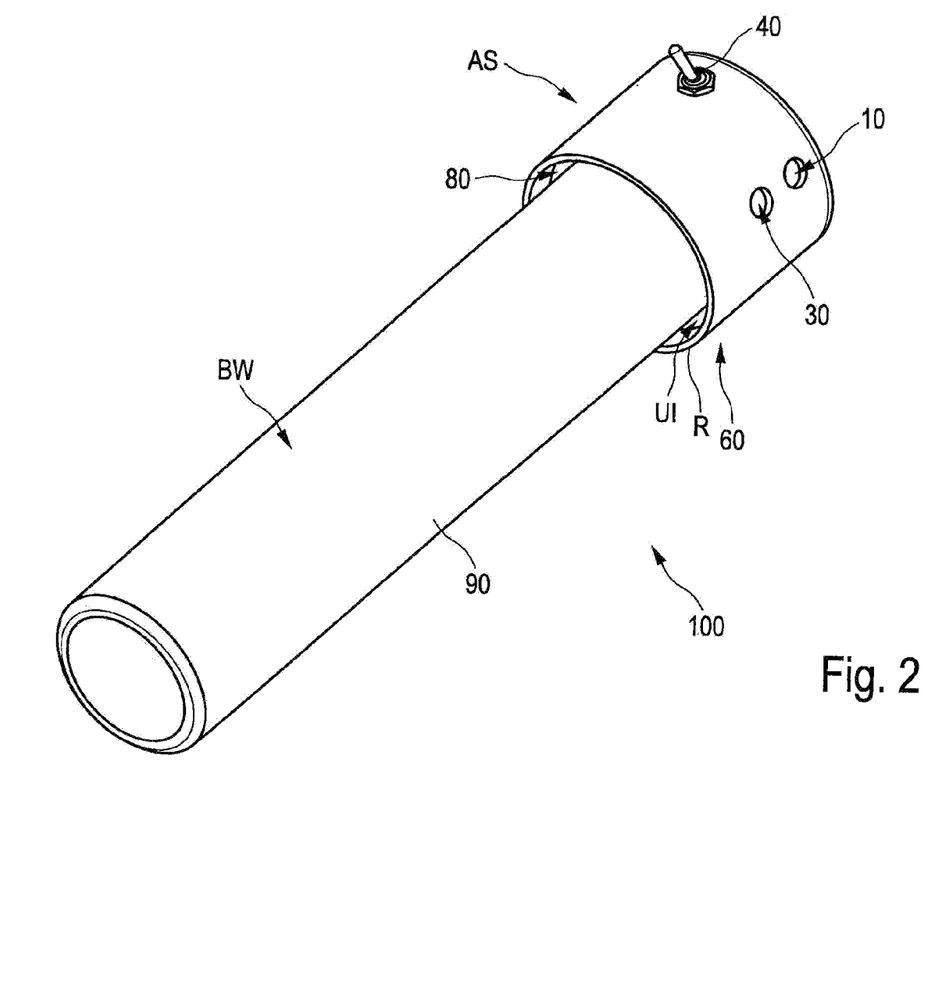
FIG. 2 is a further representation of the service water supply unit from FIG. 1.

The service water supply unit 100 is shown in greater detail in FIG. 2. The service water supply unit 100 comprises a cylindrical lid part 60. A compressed air inlet 10 for connecting the service water supply unit 100 to a compressed air source 300 (cf. FIG. 1) is arranged on the lid part 60. A service water port 30 is furthermore provided on the cylindrical lid part 60, via which port the service water can be dispensed to a medical treatment unit 200 (cf. FIG. 1).

The service water supply unit 100 comprises a vessel receptacle 80 on which, in the exemplary embodiment represented here, is arranged a cylindrical pressurized water vessel 90. The biocide-containing service water BW which is to be output via the service water port 30 is placed in the pressurized water vessel 90. By means of a switch 40 provided in the cylindrical lid part 60, compressed air present at the compressed air inlet 10 can be released and the service water BW provided in the service water vessel 90 can be discharged from the service water port 30 by means of compressed air DL.

Figure 3:
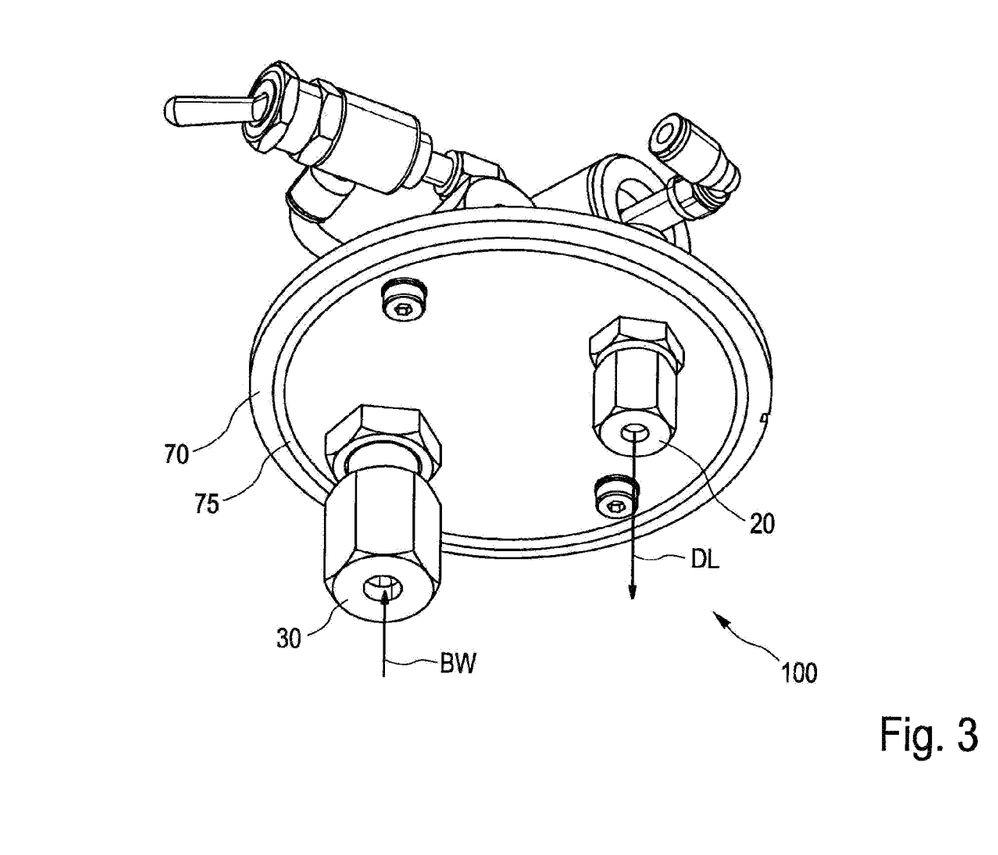
FIG. 3 shows the service water supply unit 100 of FIG. 2 viewed from below.

FIG. 3 shows the service water supply unit 100 of FIG. 2 viewed from below, i.e. observed from the direction of the pressurized water vessel 90. The portions of the compressed air port 20 and of the service water port 30 which project into the pressurized water vessel 90 (when fitted) are clearly visible on the underside of the plate-shaped base plate 70. The direction of flow of the compressed air DL and the direction of flow of the process water BW are indicated by the direction of the arrows.

Figure 4:
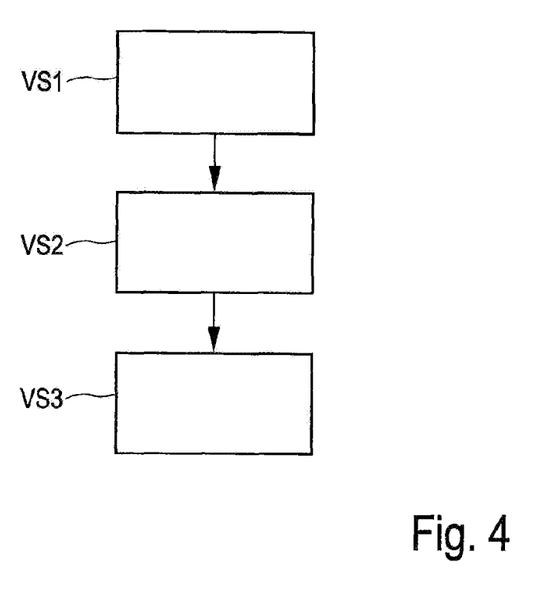
FIG. 4 is a schematic representation of a method according to the invention for treating a service water supply unit of a dental treatment unit.

FIG. 4 shows a schematic representation of a method according to the invention for treating a service water supply unit of a dental treatment unit. The method is carried out manually. The method is not restricted to application to a service water supply unit as shown in FIGS. 1 and 2. The method will, however, be described below by way of example with reference to the service water supply unit 100 shown in FIGS. 1 and 2.

First of all, the pressurized water vessel 90 (cf. FIG. 2) is removed from the vessel receptacle 80.

A first treatment step VS1 involves cleaning the service water supply unit using a cleaning agent. By way of example, cleaning in the first treatment step VS1 is carried out using a liquid, alkaline cleaning agent with a pH of 8.

Cleaning proceeds at least in part mechanically and includes scrubbing which is repeated a number of times. The first treatment step VS1 involves cleaning both the vessel receptacle 80 and the pressurized water vessel 90 (cf. FIG. 2) by means of the cleaning liquid, wherein only the pressurized water vessel 90 is cleaned within a cleaning tank.

A subsequent second treatment step VS2 involves rinsing off by means of a rinsing liquid any residues of the cleaning agent used during the mechanical cleaning after the mechanical cleaning. The rinsing liquid is autoclaved water. The second treatment step VS2 involves rinsing off of both the vessel receptacle 80 and the pressurized water vessel 90 (cf. FIG. 2) by means of the autoclaved water.

A subsequent third treatment step VS3 involves disinfecting the service water supply unit using a disinfecting agent. The third treatment step VS3 involves disinfecting the pressurized water vessel 90 by way of example by means of immersion disinfection in a disinfecting liquid which contains dimethoxytetrahydrofuran. The vessel receptacle 80 (cf. FIG. 2) is disinfected by means of the disinfecting agent by wiping.

In order to avoid recontamination, the vessel receptacle 80 is advantageously cleaned firstly on the lower inner side UI (cf. FIG. 2) and from there outwards to the edge R of the vessel receptacle 80. An outer side AS can then be cleaned. The vessel receptacle 80 components required for conveying water, which in proper operation project into the pressurized water vessel 90, then follow. These are (cf. FIG. 3) the compressed air port 20 and the service water port 30. The vessel receptacle 80 is advantageously disinfected in the same order.

Figure 5:
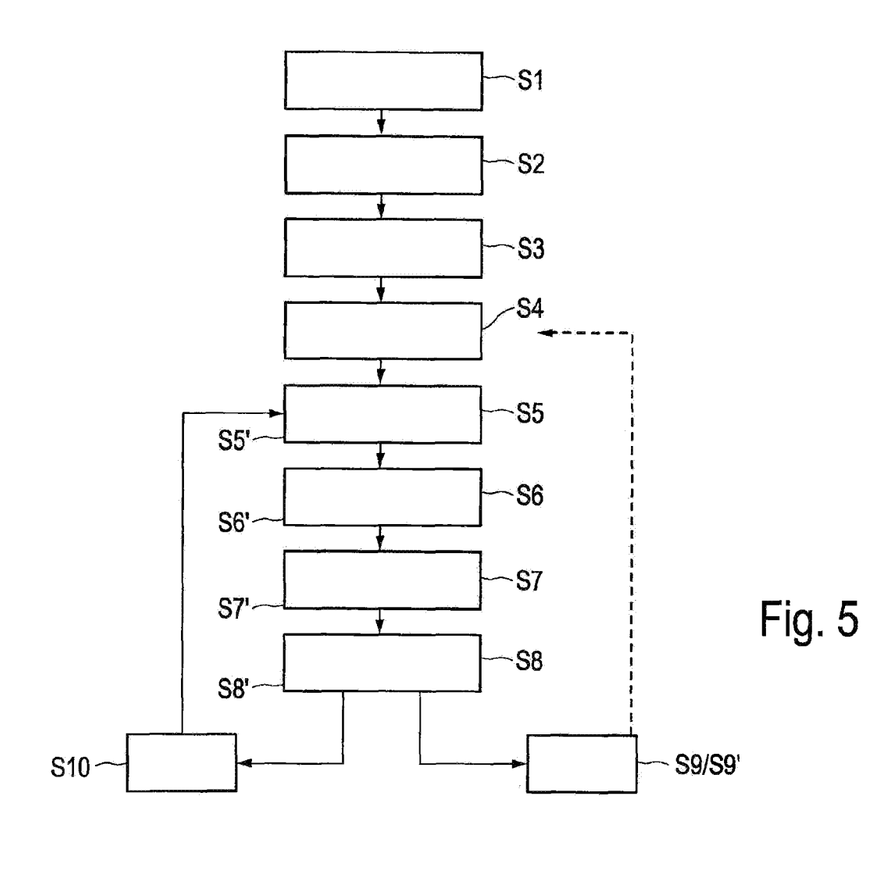
FIG. 5 is a schematic representation of a method according to the invention for defining a sequence of treatment steps for treating a service water supply unit of a dental treatment unit.

FIG. 5 shows a schematic representation of a method according to the invention for defining a sequence of treatment steps for treating a service water supply unit of a dental treatment unit.

A first step S1 involves providing a service water supply unit of a dental treatment unit, for example a service water supply unit 100 as shown in FIG. 2.

A second step S2 involves specifying a group of defined test points. The group of defined test points includes the following test points: internal walls of tubes, internal faces of tanks, external faces of tanks, disinfecting agent metering system, seals, valves, filters, particulate filters, retrogradely contaminable/contaminated open vessel systems, retrogradely contaminable/contaminated tube systems, grooves, indentations, connectors, receiving devices, closures, inner walls of vessels, inner walls of pressure vessels, outer walls of vessels, outer walls of pressure vessels, threaded closures, threaded connectors, threads, push fittings, valve membranes, pumps, pump membranes, dead flow zones, surfaces, nozzles or push-fit nozzles.

A third step S3 involves selecting a plurality of test points actually present on the service water supply unit from the specified group of defined test points. In the present exemplary embodiment, the method is described by way of example on the basis of the service water supply unit 100 shown in FIG. 2.

The service water supply unit 100 shown in FIG. 2 has a pressurized water vessel 90. The test points selected from the group of defined test points are accordingly the inner walls and the outer walls of the pressure vessel. This selection, which forms a subgroup, is made by way of example and is not necessarily exhaustive.

The fourth step S4 involves selecting a first test point to be tested from the subgroup of the plurality of test points actually present on the service water supply unit, to which a relevance criterion applies. The relevance criterion in the present case is "water-conveying". An inner wall of the pressure vessel is accordingly selected as the first test point to be tested.

A fifth step S5 involves applying a defined test soil, by way of example a protein test soil, to the first test point to be tested, namely the inner wall of the pressure vessel.

A sixth step S6 involves subjecting the first test point to be tested to a cleaning step which is selected from a specified group of treatment steps, wherein the cleaning step is carried out with a specified cleaning duration and a specified cleaning intensity. Cleaning proceeds by way of example with a liquid, alkaline cleaning agent with a pH of 8. Cleaning here proceeds at least in part mechanically and includes scrubbing which is not repeated.

A seventh step S7 involves subjecting the first test point to be tested to a disinfection step which is selected from the specified group of treatment steps, wherein the disinfection step is carried out with a specified disinfection duration and a specified disinfection concentration. By way of example, the pressurized water vessel and thus the test point "inner wall of the pressure vessel" is disinfected by means of immersion disinfection for 5 minutes in a disinfecting liquid which contains 5% dimethoxytetrahydrofuran. An eighth step S8 involves detecting a reduction in the test soil at the test point.

A ninth step S9 involves documenting or saving the sequence of the cleaning step carried out with a specified cleaning duration and a specified cleaning intensity and the disinfection step carried out with a specified disinfection duration and a specified disinfection concentration, preferably in a database, if the detected reduction falls below a specified threshold.

By way of example, a reduction by 5 log steps should apply as the specified threshold. Since cleaning in the sixth step S6 is carried out by scrubbing without repetition, the specified reduction by 5 log steps in the protein test soil is for example not achieved.

The sequence actually carried out in the ninth step S9 is thus not saved as an advantageous sequence. The sequence actually carried out can, should a specified reduction not be achieved, be saved as an inexpedient sequence.

A tenth step S10 involves excluding the respectively selected cleaning step from the group of treatment steps, since the detected reduction does not fall below a specified threshold. By way of example, a single mechanical scrubbing is excluded from the group of treatment steps.

It is explained below by way of example how the method can be carried out iteratively. A further step S5' involves once again applying a defined test soil, namely the protein test soil, to the first test point to be tested, in the present case the test point "inner wall of the pressure vessel". In order to ensure comparability of the measurements, a new pressure vessel is advantageously provided.

A further step S6' involves subjecting the first test point to be tested to a different or modified cleaning step which is selected from a specified group of remaining treatment steps. By way of example, the scrubbing step should be modified by being repeated three times.

A further step S8' involves detecting a reduction in the test soil at the test point. By way of example, a reduction by 5 log steps should apply as the specified threshold. Since cleaning in the further step S6' is carried out by scrubbing with three repeats, the specified reduction by 5 log steps in the protein test soil is for example achieved.

A further step S9' involves documenting or saving the sequence of the cleaning step carried out with a specified cleaning duration and a specified cleaning intensity and the disinfection step carried out with a specified disinfection duration and a specified disinfection concentration, preferably in a database, since the detected reduction falls below the specified threshold.

A second test point to be tested can then be selected from the subgroup of the plurality of test points actually present on the service water supply unit, for example for the test point "outer walls of the pressure vessel" to which the relevance criterion contact with water spray applies. This is shown by way of example in FIG. 4 by the dashed arrow pointing to the selection step S4.

Figure 6:
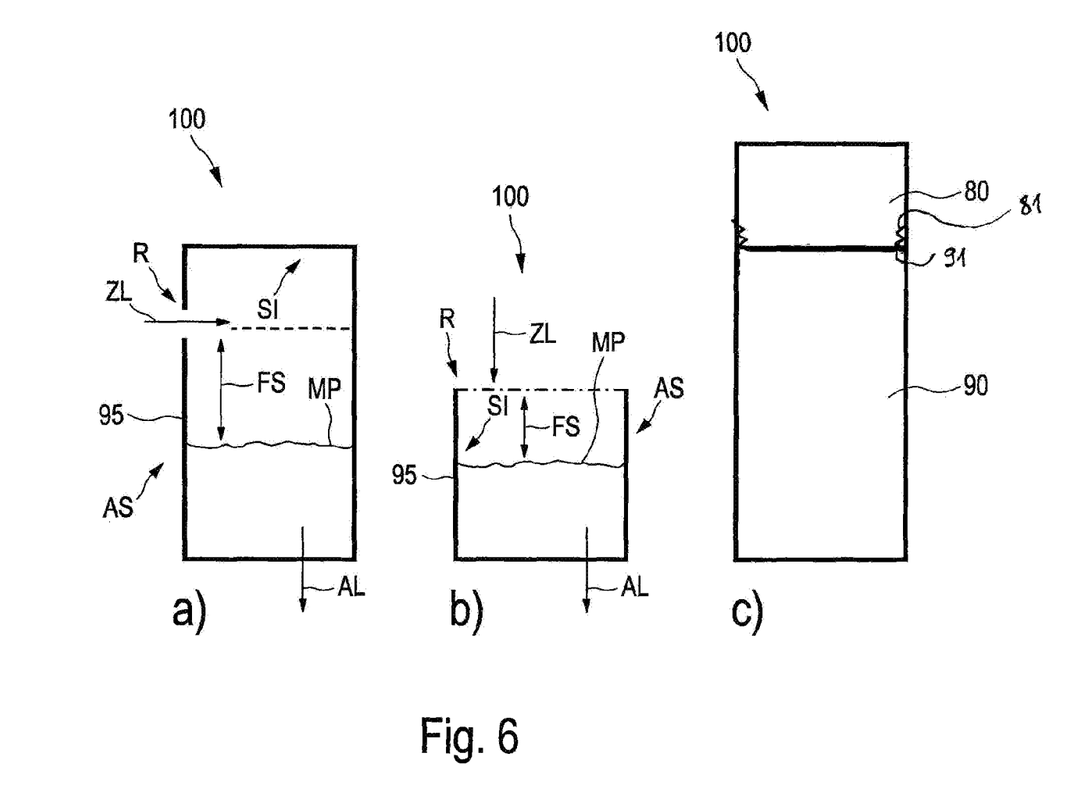
FIG. 6 is a schematic representation of three service water supply units.

FIG. 6 shows a schematic representation of three service water supply units 100 to which the treatment method according to the invention can be applied. FIGS. 6a) and b) show a service water supply unit 100 as a free outlet with an unpressurized vessel 95 (service water reservoir) which can be arranged outside or within the supplied dental treatment unit. FIG. 6c) is a schematic diagram of the service water supply unit 100 which has already been described with reference to FIG. 2. As is apparent from FIG. 6c), the pressurized water vessel 90 has an external thread 91. The vessel receptacle 80 has an internal thread 81. The external thread 91 can be completely covered by the vessel receptacle 80.

The vessel 95 in FIGS. 6a) and b) has an inlet ZL on the drinking water installation side and an outlet AL to the dental treatment unit. A respective maximum service water level MP in the vessel 95 is symbolized by a wavy horizontal line. An unimpeded free flow section FS is symbolized by the vertical arrow. In order to avoid recontamination, the vessel 95 of the service water supply unit 100 is advantageously cleaned firstly on the inner side SI (cf. FIG. 2) and from there outwards to the edge R of the vessel 95. An outer side AS can then be cleaned. The vessel 95 is advantageously disinfected in the same order.

Figure 7:
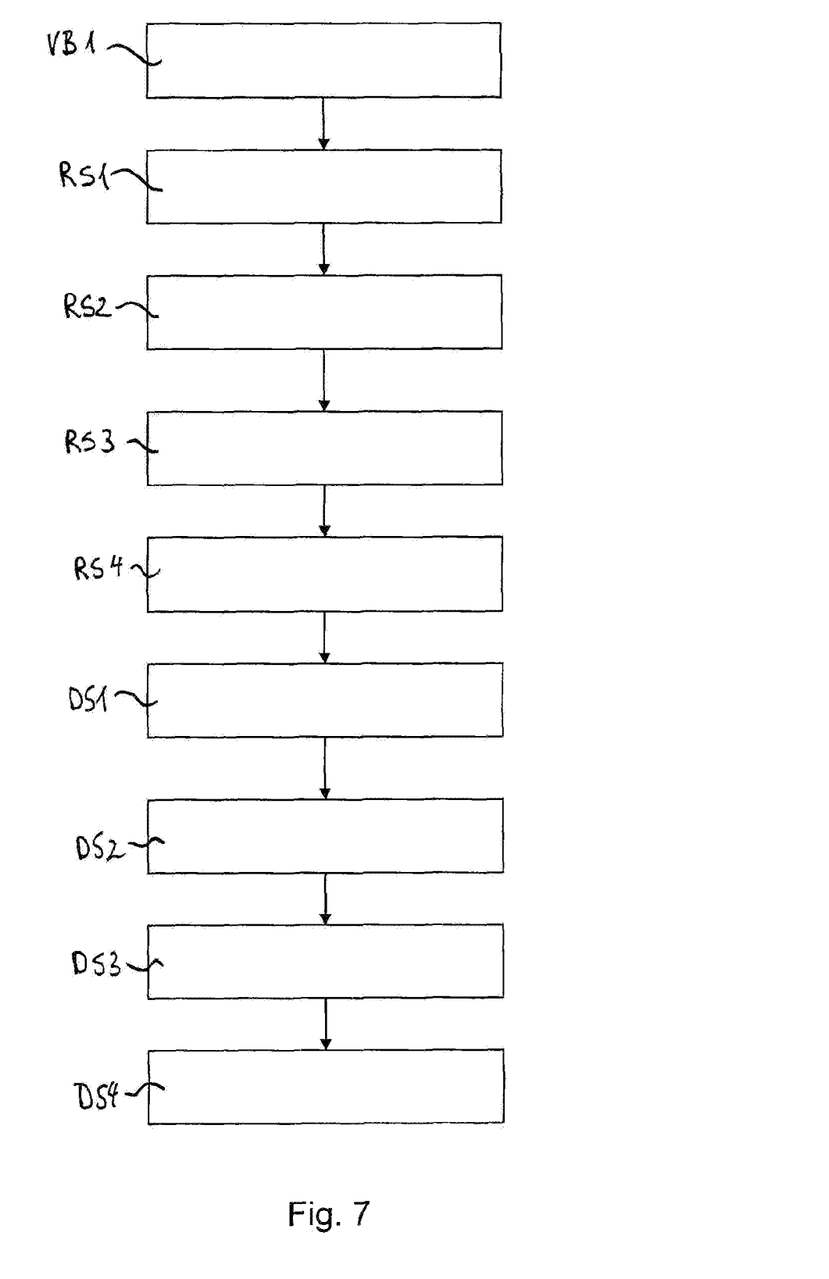
FIG. 7 is a schematic representation of a first particularly preferred exemplary embodiment of a method according to the invention for treating a service water supply unit of a dental treatment unit.

FIG. 7 shows a schematic representation of a first particularly preferred exemplary embodiment of a method according to the invention for treating a service water supply unit of a dental treatment unit. The method is carried out on a service water supply unit in the form of a "bottle" system 100 (cf. FIG. 2 and FIG. 6c). The pressurized water vessel receptacle is also referred to as the head.

A preparation step VB1 involves impregnating or providing at least one cloth with a mildly alkaline cleaning agent (cleaning cloth). At least one cloth is likewise impregnated or provided with an alcohol-based disinfecting agent (disinfecting agent cloth). The preparation step VB1 likewise involves removing the pressurized water vessel 90 (cf. FIG. 2) from the head (cf. FIG. 2 pressurized water vessel receptacle 80) of the bottle system, and completely emptying the pressurized water vessel of any liquid residues remaining in the vessel.

A first cleaning sequence RS1 of the bottle system involves cleaning the threads in the head and pressure vessel, namely the internal thread 81 and the external thread 91 (cf. FIG. 6c). To this end, a cleaning cloth is picked up and, preferably completely unfolded, passed from below beneath the head which locks the pressure vessel with a thread (internal thread 81). The cleaning cloth is placed upwards on the head with the lateral thread (internal thread 81). The cleaning cloth here completely covers the bottom and the lateral thread. The cleaning cloth is then held in place and the emptied pressure vessel (pressurized water vessel 90) is then slowly screwed from below back onto the head in order to clean the interspaces by a horizontal and vertical mechanical movement of the cleaning cloth. The screwed-on pressure vessel is then slowly undone in order to enhance the effect once again with oppositely acting mechanical forces. The first cleaning sequence RS1 is preferably repeated 3× in each case with a new cloth.

A second cleaning sequence RS2 involves cleaning the head underside of the pressure vessel receptacle. To this end, using a new cleaning cloth, the underside of the head is cleaned in a radial movement starting from the outer edge towards the middle of the face. The face should be taken to mean the underside of the base plate 70 visible in FIG. 3. Using the cleaning cloth, a slot (cf. FIG. 3, slot 75) between the end of the riser tube and the underside of the head is wiped 360° right around. The second cleaning sequence RS2 is preferably repeated 3× with an unused part of the cloth or with a new one.

A third cleaning sequence RS3 involves internally cleaning the pressure vessel (cf. FIG. 2 pressurized water vessel 90). To this end, a new cleaning cloth is picked up and the emptied pressure vessel is held overhead (with the opening downwards) in one hand and the completely unfolded cleaning cloth is placed with the other hand on the lower interior edge of the cylindrical vessel. Using a radial wiping movement encompassing 360°, the vessel is cleaned internally from bottom to top (up to the highest point). The upper edge of the opening of the pressure vessel is completely wiped in one movement with the unused side of the cloth. The third cleaning sequence RS3 is preferably repeated 3×.

A fourth cleaning sequence RS4 involves externally cleaning the pressure vessel. To this end, a new cleaning cloth is picked up and the emptied pressure vessel is held externally in one hand with the opening downwards and the completely unfolded cleaning cloth is placed with the other hand on the upper closed outer end of the cylindrical vessel and, using a radial wiping movement encompassing 360°, the vessel is cleaned externally from top to bottom. The fourth cleaning sequence RS4 is preferably repeated 3×.

A subsequent first disinfection sequence DS1 of the bottle system involves disinfecting the threads in the head and pressure vessel, namely the internal thread 81 and the external thread 91 (cf. FIG. 6c). To this end, a disinfecting agent cloth is picked up and, preferably completely unfolded, passed from below beneath the head which locks the pressure vessel and placed upwards on the head with the lateral thread. The disinfecting agent cloth here completely covers the bottom and the lateral thread. The disinfecting agent cloth is then held in place and the emptied pressure vessel is then slowly screwed from below back onto the head in order to disinfect the interspaces by a horizontal and vertical mechanical movement of the cloth. The screwed-on pressure vessel is then slowly undone in order to enhance the effect once again with oppositely acting mechanical forces. The first disinfection sequence DS1 is preferably repeated 3× in each case with a new cloth.

A second disinfection sequence DS2 involves disinfecting the head underside of the pressure vessel receptacle. To this end, using a new disinfecting agent cloth, the underside of the head is disinfected in a radial movement starting from the outer edge towards the middle of the face. The face should be taken to mean the underside of the base plate 70 visible in FIG. 3. Using the disinfecting agent cloth, a slot (cf. FIG. 3, slot 75) between the end of the riser tube and the underside of the head is wiped 360° right around. The second disinfection sequence DS2 is preferably repeated 3× with an unused part of the cloth or with a new one.

A third disinfection sequence RS3 involves internally disinfecting the pressure vessel (cf. FIG. 2 pressurized water vessel 90). To this end, a new disinfecting agent cloth is picked up and the emptied pressure vessel is held overhead (with the opening downwards) in one hand and the completely unfolded disinfecting agent cloth is placed with the other hand on the lower interior edge of the cylindrical vessel. Using a radial wiping movement encompassing 360°, the vessel is disinfected internally from bottom to top (up to the highest point). The upper edge of the opening of the pressure vessel is completely wiped in one movement with the unused side of the cloth. The third disinfection sequence DS3 is preferably repeated 3×.

A fourth disinfection sequence DS4 involves externally disinfecting the pressure vessel. To this end, a new disinfecting agent cloth is picked up and the emptied pressure vessel is held externally in one hand with the opening downwards and the completely unfolded disinfecting agent cloth is placed with the other hand on the upper closed outer end of the cylindrical vessel and, using a radial wiping movement encompassing 360°, the vessel is disinfected externally from top to bottom. The fourth disinfection sequence DS4 is preferably repeated 3×.

The described cleaning sequences RS1, RS2, RS3 and RS4 and/or the described disinfection sequences DS1, DS2, DS3 and DS4 are preferably carried out in the described order.

Figure 8:
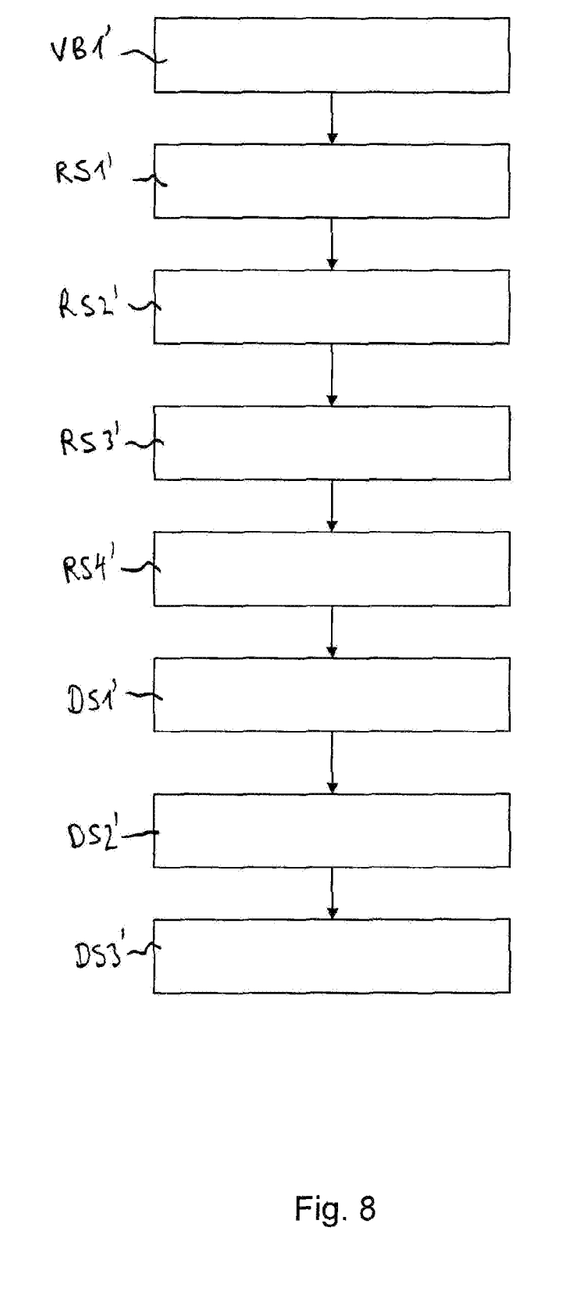
FIG. 8 is a schematic representation of a second particularly preferred exemplary embodiment of a method according to the invention for treating a service water supply unit of a dental treatment unit.

FIG. 8 shows a schematic representation of a second particularly preferred exemplary embodiment of a method according to the invention for treating a service water supply unit of a dental treatment unit. The method is carried out on a service water supply unit in the form of a "bottle" system 100 (cf. FIGS. 1 and 2 and FIG. 6c).

A preparation step VB1 involves impregnating or providing at least one cloth with a mildly alkaline cleaning agent (cleaning cloth). At least one cloth is likewise impregnated or provided with an alcohol-based disinfecting agent (disinfecting agent cloth). A mildly alkaline cleaning agent for an immersion bath and a disinfecting agent for an immersion bath are furthermore prepared. At least one brush, a sponge, and/or a(n unimpregnated) cloth are also prepared as required. The preparation step VB1 initially involves removing the pressurized water vessel 90 (cf. FIG. 2) from the head (cf. FIG. 2 pressurized water vessel receptacle 80) of the bottle system, and completely emptying the pressurized water vessel of any liquid residues remaining in the vessel.

A first cleaning sequence RS1' of the bottle system involves cleaning the threads in the head and pressure vessel, namely the internal thread 81 and the external thread 91 (cf. FIG. 6c). To this end, a cleaning cloth is picked up and, preferably completely unfolded, passed from below beneath the head which locks the pressure vessel with a thread (internal thread 81). The cleaning cloth is placed upwards on the head with the lateral thread (internal thread 81). The cleaning cloth here completely covers the bottom and the lateral thread. The cleaning cloth is then held in place and the emptied pressure vessel (pressurized water vessel 90) is then slowly screwed from below back onto the head in order to clean the interspaces by a horizontal and vertical mechanical movement of the cleaning cloth. The screwed-on pressure vessel is then slowly undone in order to enhance the effect once again with oppositely acting mechanical forces. The first cleaning sequence RS1' is preferably repeated 3× in each case with a new cloth.

A second cleaning sequence RS2' involves cleaning the head underside of the pressure vessel receptacle. To this end, using a new cleaning cloth, the underside of the head is cleaned in a radial movement starting from the outer edge towards the middle of the face. The face should be taken to mean the underside of the base plate 70 visible in FIG. 3. Using the cleaning cloth, a slot (cf. FIG. 3, slot 75) between the end of the riser tube and the underside of the head is wiped 360° right around. The second cleaning sequence RS2' is preferably repeated 3× with an unused part of the cloth or with a new one.

A third cleaning sequence RS3' involves internally cleaning the pressure vessel (cf. FIG. 2 pressurized water vessel 90). To this end, the pressure vessel is placed in the immersion bath with cleaning solution and completely immersed The completely immersed pressure vessel is cleaned internally using a brush, a sponge or a cloth with radial movements from the opening of the pressure vessel to its highest point. The third disinfection sequence DS3' is preferably repeated 3×.

A fourth cleaning sequence RS4' involves internally cleaning the pressure vessel (cf. FIG. 2 pressurized water vessel 90). The completely immersed pressure vessel is cleaned externally using a brush, a sponge or a cloth with a radial movement from the outer, closed side towards the open side. The fourth disinfection sequence DS3' is preferably repeated 3×.

A subsequent first disinfection sequence DS1' involves internally and externally disinfecting the pressure vessel. The pressure vessel is here placed in the disinfecting agent immersion bath in such a manner that the vessel is completely filled with disinfecting agent. The disinfecting agent vessel is left in the immersion bath for the stated disinfecting agent contact time. The disinfecting agent vessel is then rinsed off and dried.

A subsequent second disinfection sequence DS2' involves disinfecting the threads in the head and pressure vessel, namely the internal thread 81 and the external thread 91 (cf. FIG. 6c). To this end, a disinfecting agent cloth is picked up and, preferably completely unfolded, passed from below beneath the head which locks the pressure vessel and placed upwards on the head with the lateral thread. The disinfecting agent cloth here completely covers the bottom and the lateral thread. The disinfecting agent cloth is then held in place and the emptied pressure vessel is then slowly screwed from below back onto the head in order to disinfect the interspaces by a horizontal and vertical mechanical movement of the cloth. The screwed-on pressure vessel is then slowly undone in order to enhance the effect once again with oppositely acting mechanical forces. The second disinfection sequence DS2' is preferably repeated 3× in each case with a new cloth.

A subsequent third disinfection sequence DS3' involves disinfecting the head underside of the pressure vessel receptacle. To this end, using a new disinfecting agent cloth, the underside of the head is disinfected in a radial movement starting from the outer edge towards the middle of the face. The face should be taken to mean the underside of the base plate 70 visible in FIG. 3.

Using the disinfecting agent cloth, a slot (cf. FIG. 3, slot 75) between the end of the riser tube and the underside of the head is wiped 360° right around. Disinfection sequence DS3' is preferably repeated 3× with an unused part of the cloth or with a new one.

The described cleaning sequences RS1', RS2', RS3' and RS4 and/or the described disinfection sequences DS1', DS2' and DS3' are preferably carried out in the described order.

The invention claimed is:

1. A method, for treating a service water supply unit of a dental treatment unit, the service water supply unit comprising a pressurized water vessel, the method comprising the following steps, in order:
   (VS1) cleaning the service water supply unit, including cleaning the pressurized water vessel, using a cleaning agent,
   (VS3) disinfecting the service water supply unit, including disinfecting the pressurized water vessel, using a disinfecting agent,
wherein the disinfection of the pressurized water vessel proceeds by means of immersion disinfection and comprises the following steps:
   placing the pressurized water vessel into a disinfection tank filled with the disinfecting agent such that the pressurized water vessel is completely covered by the disinfecting agent and an interior volume of the pressurized water vessel remains free of air bubbles,
   allowing the disinfecting agent to act for a contact time, and
   removing the pressurized water vessel from the disinfection tank.

2. The method according to claim 1, wherein the service water supply unit comprises:
   a vessel receptacle for accommodating the pressurized water vessel, having a compressed air inlet for connecting the service water supply unit to a compressed air source, a compressed air port via which compressed air originating from the compressed air inlet can be introduced into the pressurized water vessel, and having a service water port via which service water which is to be delivered from the pressurized water vessel by the compressed air introduced into the pressurized water vessel can be dispensed to the dental treatment unit,
and wherein the sequence of treatment steps further comprises:
   cleaning the vessel receptacle using a cleaning agent
   disinfecting the vessel receptacle using a disinfecting agent.

3. The method according to claim 1, wherein the cleaning, at least in part, proceeds mechanically by way of at least one of wiping, scrubbing, and brushing.

4. The method according to claim 1, wherein the cleaning proceeds with a flowing or stationary cleaning agent.

5. The method according to claim 1 further comprising the step of:
   (VS2) rinsing off any residues of the cleaning agent used during the cleaning and before the disinfection by means of a rinsing liquid.

6. The method according to claim 5, wherein the rinsing liquid is sterile and chosen from the group consisting of autoclaved water, filtered water, distilled water, bidistilled water, and deionized water.

7. The method according to claim 1, wherein the disinfecting agent intended for internal disinfection is selected from the group consisting of one or more of: aldehydes, aldehyde releasers, alkylamines or alkylamine derivatives, amphoteric surfactants, inorganic acids, chlorine-releasing compounds, chloramides, glycol derivatives, guanidines or guanidine derivatives, iodine-releasing compounds, alkalies, organic acids, peroxide compounds, phenols or phenol derivatives, phenol ethers, pyridine derivatives, quaternary compounds, heavy metal compounds, metal compounds, and thiocyanates.

8. The method according to claim 1, wherein the disinfection of the pressurized water vessel proceeds by means of external spraying or wiping disinfection and comprises one or more of the following steps:
spraying an exterior surface of the pressurized water vessel with the disinfecting agent and allowing the disinfecting agent to act for a contact time, and
wiping the exterior surface of the pressurized water vessel by means of a cloth, rag or sponge or by means of a brush, impregnated or provided with the disinfecting agent.

9. The method according to claim 2, wherein, during cleaning and/or during disinfection of the vessel receptacle,
an interior underside of the vessel receptacle, which underside in proper operation faces the pressurized water vessel and from which the service water port projects, is treated,
an interior side face of the vessel receptacle, which in operation faces the pressurized water vessel and rests against the same and does not include the service water port, is treated, and
the service water port and the compressed air port are treated.

10. The method according to claim 2, wherein, during cleaning and/or during disinfection of the pressurized water vessel,
an exterior face of the pressurized water vessel, which face in operation faces the vessel receptacle and into which the service water port projects, is treated,
an exterior side face of the pressurized water vessel, which side face in proper operation faces the pressurized water vessel and rests against the same, is treated, and
an interior volume of the pressurized water vessel is treated, beginning with an interior bottom of the pressurized water vessel.

11. The method according to claim 1, wherein the sequence of treatment steps is repeated after at most one month of operation.

12. The method according to claim 2, wherein the cleaning in part proceeds mechanically and includes wiping, and the disinfection proceeds solely by means of wiping disinfection,
wherein the cleaning comprises a first cleaning sequence (RS1) involving cleaning a thread of the vessel receptacle and of the pressurized water vessel, a subsequent second cleaning sequence (RS2) involving cleaning a head underside of the vessel receptacle, a subsequent third cleaning sequence (RS3) involving internally cleaning the pressurized water vessel, and a subsequent fourth cleaning sequence (RS4) involving externally cleaning the pressurized water vessel, and
the subsequent disinfection comprises a first disinfection sequence (DS1) involving disinfecting the thread of the vessel receptacle and of the pressurized water vessel, a subsequent second disinfection sequence (DS2) involving disinfecting the head underside of the vessel receptacle, a subsequent third disinfection sequence (DS3) involving internally disinfecting the pressurized water vessel and a subsequent fourth disinfection sequence (DS4) involving externally disinfecting the pressurized water vessel.

13. The method according to claim 2, wherein the cleaning in part proceeds mechanically and includes wiping, the cleaning includes immersion bath cleaning, and the disinfection proceeds by means of wiping disinfection and by means of immersion disinfection,
wherein the cleaning comprises a first cleaning sequence (RS1') involving cleaning a thread of the vessel receptacle and of the pressurized water vessel, a subsequent second cleaning sequence (RS2') involving cleaning a head underside of the vessel receptacle, a subsequent third cleaning sequence (RS3') involving internal immersion bath cleaning of the pressurized water vessel, and a subsequent fourth cleaning sequence (RS4') involving external immersion bath cleaning of the pressurized water vessel, and
the subsequent disinfection comprises a first disinfection sequence (DS1') involving internally and externally disinfecting the pressurized water vessel in the immersion bath, a subsequent second disinfection sequence (DS2') involving disinfecting the thread of the head and pressurized water vessel by means of wiping disinfection, and a subsequent third disinfection sequence (DS3') involving disinfecting the head underside of the vessel receptacle by means of wiping disinfection.

* * * * *